United States Patent [19]

Bruttmann et al.

[11] Patent Number: 5,244,663

[45] Date of Patent: Sep. 14, 1993

[54] THERAPEUTIC METHOD AGAINST ALLERGY

[75] Inventors: Georges Bruttmann, Grenoble; Patrick Pedrali, Annecy, both of France; Serge Robert, Braine la chateau, Belgium

[73] Assignee: Medibrevex, Grenoble, France

[21] Appl. No.: 654,977

[22] Filed: Feb. 14, 1991

Related U.S. Application Data

[63] Continuation-in-part of Ser. No. 415,379, Sep. 29, 1989, abandoned, which is a continuation of Ser. No. 149,499, Jan. 28, 1988, abandoned.

[30] Foreign Application Priority Data

Jan. 28, 1987 [FR] France .................. 87 01378

[51] Int. Cl.$^5$ .......................... A61K 9/20; A61K 9/48; A61K 47/26
[52] U.S. Cl. ........................................ 424/400; 424/88; 424/91; 424/434; 424/435; 436/823; 436/529; 514/960; 530/329
[58] Field of Search ................. 424/91, 88, 400, 434, 424/435; 530/329; 436/823, 529; 514/960

[56] References Cited

U.S. PATENT DOCUMENTS

| | | | |
|---|---|---|---|
| 4,171,299 | 10/1979 | Hamburger | 530/329 |
| 4,364,938 | 12/1982 | Hoek | 424/88 |
| 4,642,232 | 2/1987 | Yman | 424/19 |
| 5,080,903 | 1/1992 | Ayache et al. | 424/433 |

FOREIGN PATENT DOCUMENTS 2099698 12/1982 United Kingdom .

Primary Examiner—Thurman K. Page
Assistant Examiner—Robert H. Harrison
Attorney, Agent, or Firm—Browdy and Neimark

[57] ABSTRACT

Allergens are contained in strictly controlled and reproducible amounts on solid supports to provide a progressive release of the allergen perlingually and sublingually. The compositions are prepared by dissolving an allergen in a polar solvent to obtain a mother solution; preparing dilutions of different predetermined concentrations; fractionating each of the dilutions into sub-dilutions; and impregnating a pharmaceutically acceptable solid support with each sub-dilution, each impregnation step being followed by drying in forced, dried air at a temperature not greater than 30° C.; and applying a protective coating onto the composition.

11 Claims, No Drawings

THERAPEUTIC METHOD AGAINST ALLERGY

This is a continuation-in-part of application Ser. No. 07/415,379, filed Sep. 29, 1989, abandoned, which is a continuation of application Ser. No. 07/149,499, filed Jan. 28, 1988, abandoned.

FIELD OF THE INVENTION

The invention relates to a therapeutic method against allergy, consisting in administering to the patient at subsequent or successive periods respectively increasing doses of at least one allergen, so as to desensitize same patient to this allergen.

BACKGROUND OF THE INVENTION

Several desensitizing techniques have already been proposed.

According to document GB-A-2 099 698 (Melillo), it has been proposed to incorporate an allergen in small particles of some tenth microns of a pharmaceutically acceptable, in particular non-allergenic per se, solid excipient, for instance lactose; then these particles are encapsulated into calibrated capsules, for instance gelatine capsules. These capsules are intended and adapted for an administration only by inhalation, either by an inhaler tube or a nasal spray. This is the nasal way of administration of an allergen.

This way of administration has the following drawbacks:
- the quantity of the allergen actually transferred to the target organ, e.g the lungs cannot be precisely controlled
- it remains a cumbersome method requiring a fixed inhalation apparatus, and thus cannot be an ambulatory treatment.

According to document EP-A-0 135 022 (MORAN), it has been proposed to incorporate an allergen into particles of a solid excipient consisting of an acid insoluble polymer. Such a solid dispersion of the allergen is intended only for an oral administration to the target organ or cells, through the gastro-enteric path.

This way of administration of an allergen suffers from the following drawbacks:
- it is mandatory to use very high concentrations of the allergen, since a relatively important part of the latter is destroyed in the gastro-enteric path
- such concentrations may result in adverse side effects, such as gastro-intestinal upsets
- finally, it cannot be determined or controlled what is the amount actually absorbed of the antigen, and thus it is difficult to establish an exact dosage of the latter.

Further, stress has been given to the interest that a sublingual application can offer (Glenis, K. et al, *Clinical Allergy*, 1986, Vol. 16, 483–491) which would make it possible to avoid certain secondary effects of administration of the allergen by injection.

However, the galenic form selected (liquid form) is not entirely satisfactory; when relatively large dosages (i.e., volumes) are reached, a certain part of the liquid is absorbed orally and therefore escapes sublingual application, which make it impossible to control all the treatment factors. Therefore, this is a galenic form assuring very approximate dosages.

However, this method of administration sublingually seems very promising because the salivary IgA should play an important role in the effectiveness of the treatment. The mechanism of desensitizing sublingually, moreover, is approximately the same as that of desensitizing by injection.

SUMMARY OF THE INVENTION

The inventors therefore have devoted all their efforts to studying a new method for administering allergens, making it possible to benefit from all the advantages of the mode of administration perlingually and sublingually, but without having the drawbacks mentioned above.

They were able to develop a desensitizing method, ensuring a progressive and rigorous dosage of the allergen, which therefore makes it possible to assure a rigorous monitoring of the treatment. Further, the inventors were able to determine, which is quite surprising, that this new therapeutic method for application perlingually and sublingually makes it possible to obtain a much faster desensitizing than that which can be obtained by using other known ways of administration of allergens, whether it is administration by injection, orally, or perlingually with an excipient or support that is a liquid.

The therapeutic method according to the invention comprises:
- obtaining respectively different solid doses of said allergen, each dose comprising a pharmaceutically acceptable excipient in solid form formulated so as to be disintegrated in less than 5 minutes in the sublingual cavity under the action of saliva, and a controlled fractionated quantity in said allergen, said doses being identical to one another by the excipient, but differing respectively from one another by their fractionated quantities in said allergen
- conditioning in a same package respectively different solid doses of said allergen, ranging progressively by their respective contents in said allergen from a lower concentration in said allergen to a higher concentration in the latter
- providing several different packages of said solid doses, respectively increasing the dosage in said allergen, the higher concentration of one package of lower dosage being below or equal to the lower concentration of the following package of higher dosage
- administering said packages of increasing dosages, at respectively subsequent periods of the treatment, by placing each dose in solid form in the sublingual cavity, and then spitting out, the saliva having dissolved in same cavity the excipient with said allergen.

With respect to the excipient in solid form, its components, their concentrations and physical state, and the way of admixing them, are choosen according to the usual practice of the pharmacologist, so as to obtain a disintegration time of less than 5 minutes, preferably 2 to 3 minutes, in the environment and conditions of the sublingual cavity.

This invention is also characterized by the following auxiliary features.

The excipient in solid form may be a calibrated tablet or discrete particles, such as grains, contained in a calibrated capsule.

Each package of a given dosage of said allergen contains for at least one concentration of said allergen, several, for instance four identical solid doses having the same corresponding fractionated quantity in said allergen.

Each package comprises at least four different concentrations of said allergen, that is at least four different solid doses of said allergen, having fractionated quantities of said allergen respectively increasing by a fixed concentration increment, for instance ¼ of a given concentration, over the precedent.

The different packages bring respectively overall increasing dosages of said allergen. To this end, the concentration of the higher solid dose of a package of higher dosage is a multiple, for instance by ten, of the concentration of the higher solid dose of the precedent package of lower dosage.

So as to obtain the respectively different solid doses of said allergen:

said allergen is dissolved or suspended into a solvent, so as to obtain a mother solution having a reference concentration in said allergen successive dilutions of said mother solutions are prepared so as to obtain respectively different diluted solutions having respectively decreasing controlled sub-concentrations in said allergen for each respective diluted solution, sub-dilutions are prepared so as to obtain respectively different sub-diluted solutions having respectively decreasing controlled fractionated concentrations in said allergen incorporating said different fractionated sub-dilutions into respectively different lots of said solid excipient, so as to obtain said respectively different solid doses of said allergen.

The fractionated sub-dilutions are incorporated into respectively separate lots of said excipient in solid form, for instance a mixture of saccharose and lactose, by a multi-impregnation or fractionated impregnation, each impregnation step being followed by drying, in forced dried air at a temperature not greater than 30° C. Preferentially, a protective coating is applied to the excipient in solid form, after the impregnation with each said fractionated sub-dilution.

Thus, as far as a desensitizing treatment is concerned, the invention brings a novel way for the allergen of acceding to the sublingual cavity, in progressive and controlled quantities. This way which may be named the solid way brings the following basic advantages:

the therapeutic treatment may be effected with no stress or medical help once the solid excipient has been disintegrated it leaves a precise quantity of the allergen within the mouth, without any action or manipulation of the patient once prepared, no solvent or extraneous matter remains on the particles or tablets of allergen the patient may control and monitor his treatment himself, in cooperation with his physician.

This method according to the invention has also brought some specific pharmaceutical effects, for some allergens, which dispensed by other methods do not exhibit such effects. These effects are mainly:

generally speaking, no adverse reaction accelerated or faster clinical action one reproducible and effective transfer to the blood, for a predetermined dose of the allergen.

DETAILED DESCRIPTION OF THE INVENTION

The method for obtaining the solid forms of allergens according to the invention will now be described in detail.

The starting product is a lyophilized allergen. This allergen can be of any type: household dust, acarica, hymenoptera, pollen of Graminaceae or other, whether they are pneumallergens or microbial or food allergens.

The lyophilized allergen is put in solution in any suitable solvent to obtain a mother solution at 100 IR (index of reaction). The solvent used can be water or physiological serum; it can also be selected from other solvents, preferably polar solvents, such as low strength ethyl alcohol.

By IR or index of reaction is meant a measure of the quantity of the allergen in a solvent or in solid form, or on a solid support, obtained as follows:

an extract of said allergen is standardized as a reference quantity by in vivo tests made on a population of thirty patients who have proved to be allergic to same allergen; this reference quantity is the quantity of said allergen which, once inoculated by a trans-epidermal injection on the anterior face of one fore-arm, induces where injected a papula having the same dimensions as the papula induced in the same way by a titrated solution of codeine phosphate, having a weight concentration of 9% then the various samples of same allergen are titrated versus this reference quantity by the so-called RAST-inhibition technique (see method of Yman L. and coll., Develop. Biol. Standard., Karger Basel, Vol. 29, pages 151–165, 1975)

when the activity of the sample, titrated by above method is the same as the reference quantity, then its index of reactivity is 100 IR.

Then, using the same solvent as that which served to obtain the mother solution, successive dilutions at 10 IR, 1 IR, 0.1 IR, 0.001 IR and 0.0001 IR are obtained.

Each of these diluted solutions is then fractionated into different sub-diluted solutions having respectively decreasing fractionated concentrations in the allergen. For instance, the diluted solution at 0.001 IR is fractionated into sub-diluted solutions having concentrations of respectively ¼×0.001 IR, 2/4×0.001 IR, ¾×0.001 IR, while keeping a solution of 4/4×0.001 IR. The sub-diluted solutions may represent another fraction, for instance a multiple of 1/15 of the concentration of the starting diluted solution.

All the precautions will be taken, during each of the dilutions or sub-dilutions, so that the amount of solvent remains constant, to perform later all impregnation of the solid excipient in an identical way.

All the so-obtained different fractionated sub-dilutions, or a calibrated portion thereof, are incorporated into respectively different lots of a same solid excipient, for instance a mixture of saccharose-lactose, in the form of globules, but the latter may be replaced by powders or tablets. The lots are different in that they are devoted respectively to different dilutions and sub-dilutions, but they are composed of the same quantity in divided form of the same excipient.

Each lot is impregnated with a given dilution, or sub-dilution, in a manner known per se, for instance with a "spray doser" injector.

Thus, the technique of impregnation is that of multi-impregnation or fractionated impregnation to guarantee a perfect distribution of the homogeneous allergen of the various globules of the excipient.

Between each impregnation, drying is performed by passing of forced, dried air into a chamber where low pressure prevails obtained by the difference of flow existing between this air passage and a powerful extractor.

According to an important characteristic of the invention, this drying operation is performed at a temperature not greater than 30° C. It has been determined during numerous tests performed for development of said process, that this process is no longer reliable when the temperature exceeds 38°-40° C.

The last impregnation is a protective impregnation which forms a protective coating on the granules of the solid excipient.

According to another embodiment of the process according to the invention, and to guarantee that the physiochemical integrity of the allergen is totally maintained, the various impregnation steps are performed under a nitrogen atmosphere.

The final operation consists in putting the globules thus obtained into capsules, or optionally in placing said globules or powders or tablets in elementary tubes and in completing the packaging in a standard way (blisters for the capsules, boxes for the tubes), numbering the capsules with increasing doses.

Thus the following pharmaceutical presentation of the allergen may be obtained:
- the solid doses of the allergen obtained as above, i.e. calibrated quantities of impregnayed granules contained in capsules, are distributed in five packages, for instance calender plates, according to their fractionated quantities in same allergen
- these packages represent increasing dosages of said allergen, for instance 0.001 IR, 0.01 IR, 0.1 IR, 1 IR, and 10 IR
- on each package is numbered in increasing order, for instance 1 to 16, individual casings for receiving capsules of increasing fractionated quantity in said allergen; for instance, for the package of 0.001 IR dosage, the casings 1 to 4 are allotted to the fractionated quantity ¼×0.001 IR, 5 to 8 to the fractionated quantity 2/4×0.001 IR, 9 to 12 to the fractionated quantity ¾×0.001 IR, and 13 to 16 to the quantity 0.001 IR
- and the higher concentration of one package of lower dosage, for instance 0.001 IR, is below the concentration of the following package of higher dosage, for instance ¼×0.01 IR.

With the pharmaceutical presentation, the allergen may be administered progressively, over a period ranging from forty to fifty days. For instance, during five weeks, the patient takes respectively the five packages of increasing dosage, and has four doses a day for the same fractionated quantity. For each dosage, the patient places the content of one capsule in the sublingual cavity, without swallowing; after complete disintegration of the solid excipient, for instance in less than 3 minutes, he then spits out his saliva having dissolved in the sublingual cavity the excipient with the allergen.

After such a treatment, the patient may take so-called stabilization doses, with one dose per day, then twice a week, then once a week.

It has been found that, in a very surprising way, relative to standard desensitizing and particularly relative to desensitizing by injection, the clinical results are very much superior; and 80 to 85% improvement is noted at the end of two to three months of treatment. The production of antibodies of the IgG4 type is accelerated and the tolerance is perfect.

Only 2 to 3% of syndromic reactions have been counted; these are easily controlled by reduction or spacing of taking the doses.

Another entirely surprising advantage of the therapeutic method according to the invention is that the desensitizing period is very greatly reduced relative to other known methods. The treatment no longer lasts several years but simply some months, and especially, it is possible to attain maximum doses very rapidly, between eighty and one hundred days.

The new galenic forms of allergens according to the invention offer still other advantages, among which can be cited a considerable reduction of the densitizing cost, considering the almost disappearance of medical consultations or nurses' care. Only checking consulations in a month or two are necessary.

Double blind tests made against a placebo on more than two thousand patients confirms the above.

The experimental results are shown as follows:

| | ACARICA Results of Sublingual Desensitization of Adult Annual Rhinitis | | | | |
|---|---|---|---|---|---|
| Patients | Very Good | Good | Fair | No Effect | Results |
| Active allergen 15 | 9 | 1 | 3 | 2 | 13/15 86% |
| Placebo 15 | 0 | 1 | 0 | 14 | 1/15 6.5% |

| | POLLEN OF GRAMINACEAE Results of Pre-Season Sublingual Desensitization (30 Pollens) | | | | |
|---|---|---|---|---|---|
| Patients | Very Good | Good | Fair | No Effect | Results |
| Active allergen 15 | 9 | 3 | 0 | 3 | 12/15 80% |
| Placebo 15 | 0 | 0 | 2 | 13 | 2/15 13% |

| | ACARICA Results of Annual Sublingual Desensitization of 60 Alleragic Asthmatics | | | | |
|---|---|---|---|---|---|
| Patients | Very Good | Good | Fair | No Effect | Results |
| Active allergen 29 (1 dropped out of study) | 9 | 11 | 3 | 6 | 23/29 75% |
| Placebo 28 (2 dropped out of study) | 1 | 3 | 2 | 22 | 6/28 21.5% |

It is quite evident that this invention is no limited to the concentrations, modes of fractionating or dilutions given above by way of nonlimiting example; these concentrations, modes of fractionating and dilutions can, of course, be adapted on demand; also the saccharose-lactose support can be replaced by another pharmaceutically acceptable support or excipient.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

We claim:

1. A dosage form for treating allergies comprising an effective amount of an allergen in a solid carrier which disintegrates under the action of saliva in less than five minutes wherein said solid carrier is a mixture of saccharose and lactose.

2. The dosage form of claim 1 wherein said allergen is selected from the group consisting of household dust, acarica, hymenoptera and pollen.

3. A method for treating a patient suffering from allergy, by desensitizing said patient to at least one allergen causing said allergy, comprising administering said allergen sublingually and perlingually to said patient in a plurality of solid doses at progressively increasing concentrations of said allergen at respectively subsequent periods of treatment, each dose comprising a solid excipient which is a mixture saccharose and lactose, each dose containing a progressively increasing quantity of allergen;

providing in one package doses of said allergen ranging from a lower concentration of allergen to a higher concentration of allergen;

providing to said patient several different packages of said doses, respectively increasing to said patient the dosage of said allergen, wherein the higher concentration of one package of lower dosages is less than or equal to the lower concentration of the subsequent package of higher dosage; and administering to said patient said packages of increasing dosages over the course of the treatment by placing each dose in solid form in the sublingual cavity of said patient and dissolving the excipient to deliver the allergen to said patient.

4. The method of claim 3 wherein the solid excipient is in the form of a tablet.

5. The method of claim 3 wherein the solid excipient is in the form of discrete particles contained in a capsule.

6. The method of claim 3 wherein each package contains, for at least one concentration of allergen, more than one identical solid doses containing the same quantity of allergen.

7. The method of claim 3 wherein each package comprises at least four different doses of said allergen, said doses having quantities of said allergen which increase by a fixed increment over the preceding dose.

8. The method of claim 3 wherein the concentration of the higher dose of a package of higher dosage is a multiple of the concentration of the higher dose of the preceding package of lower dosage.

9. A method according to claim 3, wherein so as to obtain the respectively different solid doses of said allergen:

said allergen is dissolved or suspended into a polar solvent, so as to obtain a mother solution having a reference concentration in said allergen successive dilutions of said mother solutions are prepared so as to obtain respectively different diluted solutions having respectively decreasing controlled sub-concentrations in said allergen for each respective diluted solution, sub-dilutions are prepared so as to obtain respectively different sub-diluted solutions having respectively decreasing controlled fractionated concentrations in said allergen incorporating said different fractionated sub-dilutions into respectively different lots of said solid excipient, so as to obtain said respectively different solid doses of said allergen.

10. The method according to claim 9 wherein said sub-dilutions are incorporated into said lots of said solid excipient by impregnation, wherein said impregnation step is followed by drying in forced dried air at a temperature not greater than 30° C.

11. The method according to claim 9 wherein, after said solid excipient has been impregnated with allergen, a solid coating is applied to said impregnated solid excipient.

* * * * *